US012629116B2

(12) United States Patent
Sossin et al.

(10) Patent No.: US 12,629,116 B2
(45) Date of Patent: May 19, 2026

(54) SPECTRAL X-RAY MATERIAL DECOMPOSITION METHOD

(71) Applicant: KONINKLIJKE PHILIPS N.V., Eindhoven (NL)

(72) Inventors: Artur Sossin, Hamburg (DE); Bernhard Johannes Brendel, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 473 days.

(21) Appl. No.: 18/024,301

(22) PCT Filed: Aug. 31, 2021

(86) PCT No.: PCT/EP2021/073920

§ 371 (c)(1),
(2) Date: Mar. 2, 2023

(87) PCT Pub. No.: WO2022/049039

PCT Pub. Date: Mar. 10, 2022

(65) Prior Publication Data

US 2023/0309937 A1     Oct. 5, 2023

(30) Foreign Application Priority Data

Sep. 3, 2020     (EP) ..................................... 20194235

(51) Int. Cl.
A61B 6/42          (2024.01)
A61B 6/00          (2006.01)
A61B 6/03          (2006.01)

(52) U.S. Cl.
CPC ............ A61B 6/4241 (2013.01); A61B 6/032 (2013.01); A61B 6/5205 (2013.01); A61B 6/482 (2013.01)

(58) Field of Classification Search
CPC ...... G06V 10/774; G06N 3/045; G06N 3/084; A61B 6/032; A61B 6/4241; A61B 6/482; A61B 6/5205
See application file for complete search history.

(56) References Cited

U.S. PATENT DOCUMENTS 9,687,207 B2     6/2017  Zou
11,864,939 B2    1/2024  Zhou
(Continued)

FOREIGN PATENT DOCUMENTS

CN          110675467 A      1/2020
WO      WO2014167450 A1      10/2014

OTHER PUBLICATIONS

PCT International Search Report, International application No. PCT/EP2021/073920, Nov. 26, 2021.
(Continued)

*Primary Examiner* — David J Makiya
*Assistant Examiner* — Miya Downing
(74) *Attorney, Agent, or Firm* — Larry Liberchuk

(57)          ABSTRACT

A method for material decomposition of an object based on spectral X-ray scan data for the object and based on application of a frequency split approach. The method comprises using two AI models in parallel to perform the material decomposition analysis based on input spectral X-ray data, wherein the models are configured such that one exhibits higher bias and lower variance (lower noise) than the other. The input spectral X-ray data is fed to both models. The output material composition data from the low bias model is low-pass filtered and the output material composition data from the low variance model is high pass filtered. The
(Continued)

outputs from the two models are linearly combined, either before the filtering or after. The resulting combined material decomposition data has both lower bias and lower noise compared to the output generated if just one AI model were to be used.

10 Claims, 3 Drawing Sheets

(56) References Cited

U.S. PATENT DOCUMENTS

| | | | | |
|---|---|---|---|---|
| 11,886,978 | B2 | 1/2024 | Isogawa | |
| 2007/0083365 | A1* | 4/2007 | Shmunk | G10L 21/0272 |
| | | | | 704/232 |
| 2017/0200067 | A1 | 7/2017 | Zhou | |
| 2019/0102883 | A1 | 4/2019 | Flohr | |
| 2020/0196972 | A1* | 6/2020 | Zhou | A61B 6/4014 |

OTHER PUBLICATIONS

Roessl E. et al., "K-Edge Imaging in X-Ray Computed Tomography Using Multi-Bin Photon Counting Detectors", Physics in Medicine & Biology, vol. 52, No. 15, pp. 4679-4696, Aug. 2007.

Zimmerman K.C. et al., "Experimental Comparison of Empirical Material Decomposition Methods for Spectral CT", Physics in Medicine & Biology, vol. 60, pp. 3175-3191, 2015.

Alvarez R.E. et al., "Near Optimal Neural Network Estimator for Spectral X-Ray Photon Counting Data with Pileup", Medical Physic, arXiv e-print, 1702.01006, Feb. 2017.

Zhang W. et al., "Image Domain Dual Material Decomposition for Dual-Energy CT Using Butterfly Network", Medical Physics, vol. 46, Issue 5, pp. 2037-2051, 2019.

Ku Y. et al., "Image Decomposition Algorithm for Dual-Energy Computed Tomography via Fully Convolutional Network", Hindawi, Computational and Mathematical Methods in Medicine, vol. 2018, Article ID 2527516, 9 pages.

Willemink M.J. et al. "Photon-Counting CT: Technical Principles and Clinical Prospects", Radiology, vol. 289 Issue 2, pp. 293-312, 2018.

* cited by examiner

Access 1ˢᵗ (low bias) AI model and 2ⁿᵈ (low variance) AI model — 12

Obtain input spectral X-ray data — 14

Feed spectral X-ray data to 1ˢᵗ AI model to generate output material decomposition data — 16

Feed spectral X-ray data to 2ⁿᵈ AI model to generate output material decomposition data — 18

Low pass filter output from 1ˢᵗ model
High pass filter output from 2ⁿᵈ model — 20

Linearly combine outputs from 1ˢᵗ and 2ⁿᵈ AI models — 22

FIG. 1

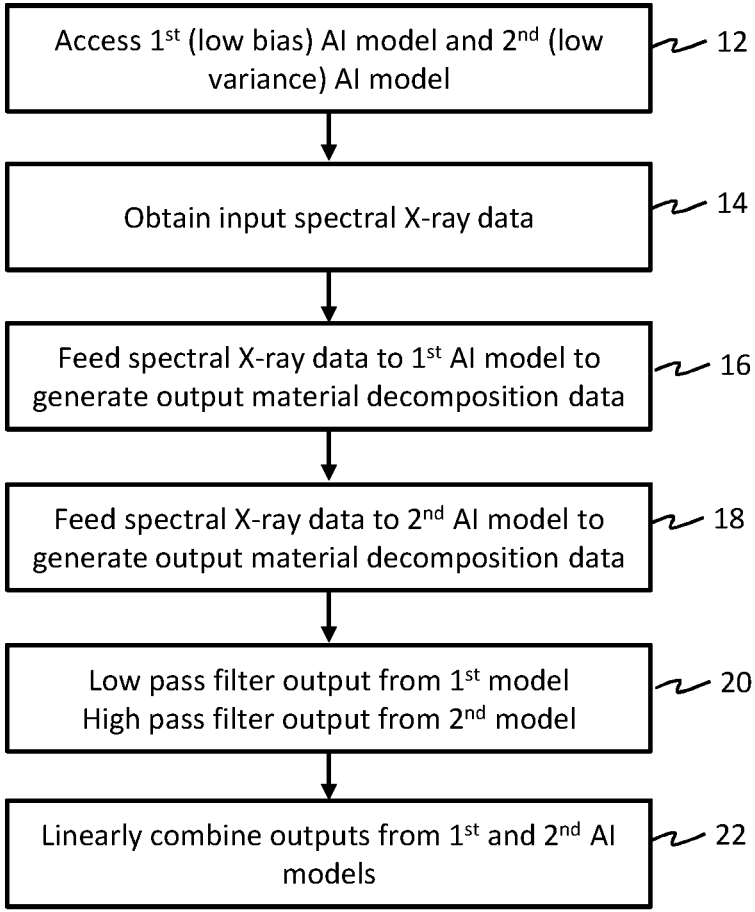
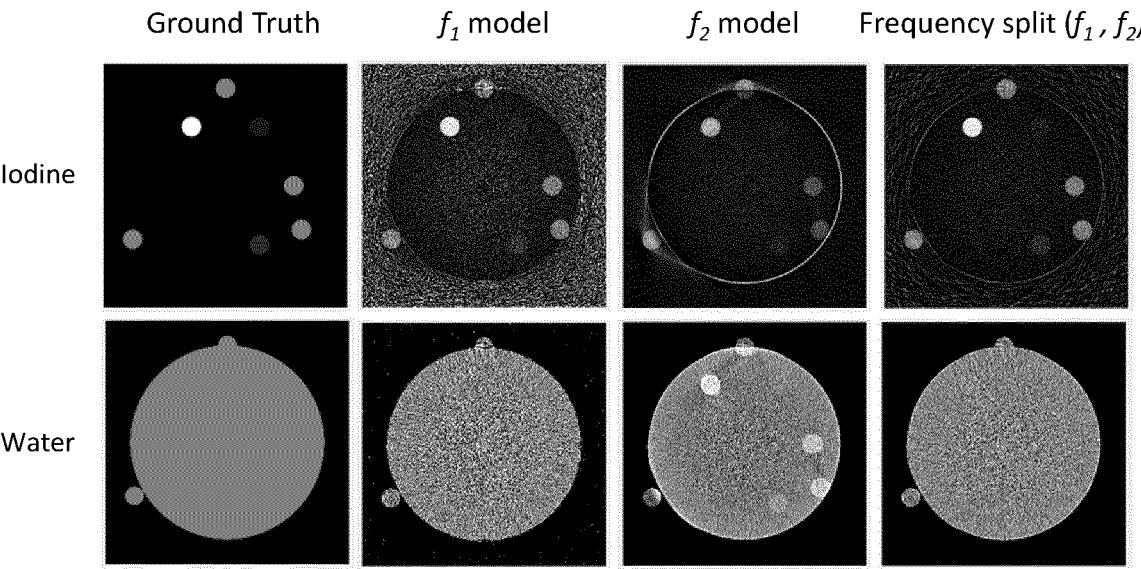

| Ground Truth | $f_1$ model | $f_2$ model | Frequency split ($f_1$, $f_2$) |

Iodine

Water

FIG. 2

Obtain preliminary AI model — 82

Obtain first and second training data, $T_1$, $T_2$, $T_1$ having reduced noise — 84

Train a first copy of AI model with first training data $T_1$ — 86

Train a second copy of AI model with second training data $T_2$ — 88

SPECTRAL X-RAY MATERIAL DECOMPOSITION METHOD

FIELD OF THE INVENTION

The present invention relates to a material decomposition method using spectral X-ray data.

BACKGROUND OF THE INVENTION

By using multi-energy X-ray detectors, it is possible to measure the spectrum of X-ray energies or frequencies received at different locations across an X-ray detector during X-ray imaging of an object. This is known as spectral X-ray imaging. Spectral X-ray data allows for discerning and quantifying materials comprised by the scanned object. It can be performed using data from conventional X-ray imaging or fluoroscopy, or using data from computed tomography (CT) imaging.

With reference first to CT imaging, a conventional computed tomography (CT) scanner includes an x-ray tube mounted on a rotatable gantry opposite one or more integrating detectors. The x-ray tube rotates around an examination region located between the x-ray tube and the one or more detectors and emits polychromatic radiation that traverses the examination region and a subject and/or object disposed in the examination region. The one or more detectors detect radiation that traverses the examination region and generate a signal, or projection data, indicative of the examination region and the subject and/or object disposed therein. The projection data is e.g. raw detector data or a projection sinogram, the latter being a visual representation of the projection data captured by the detector(s). A reconstructor is typically further used to process the projection data and reconstructs a volumetric image of the subject or object.

X-ray Spectral CT is an imaging modality that extends the capabilities of a conventional CT system by incorporating a detector which can discriminate between different X-Ray energies, e.g. an energy discriminating photon counting detector or energy integrating detector. X-Ray spectral CT allows for material decomposition of the scanned object.

In material decomposition, a forward model can be used which models the expected photon counts or expected integrated photon energies in different photon energy windows (bins) at each pixel of the detector as a function of a certain set (basis) of materials and their respective equivalent path lengths in the scanned material. To decompose the material composition of an object, this forward model can be inverted to determine the material path lengths of each of the basis materials based on the spectral projection data.

One way of doing this is to numerically invert the equation, for example using statistical estimation algorithms, such as a maximum likelihood estimation algorithm (MLE). However, this can lead to over-simplification, unable to account for real-word detector effects such as pulse pileup and charge sharing. Moreover, the MLE algorithm requires a lot of computational resource due to the iterative optimization techniques involved in finding the solution.

An alternative approach is to use an Artificial Intelligence based method. Here, AI algorithms, such as machine learning algorithms, are trained with known material path lengths and corresponding photon counts or detection signals per energy bin in order to learn the system forward model inversion. This is done prior to scanning (offline) once per material basis. An advantage of such methods is that AI-model inference is computationally less expensive then applying the MLE approach to the decomposition problem. AI-based approaches however can also lead to inaccurate results due for example to biases in the model algorithms.

Improved accuracy and reliability in AI based approaches to spectral X-ray material decomposition would be desirable.

SUMMARY OF THE INVENTION

It has been recognized by the inventors that, for an AI-based approach to the material decomposition, during the network training, a known compromise (bias-variance trade-off) must be made between the amount of noise in the material path-lengths estimated by the AI-model and the amount of bias. This results in a model that has a certain bias and a certain noise. However, the desire for a photon counting system aimed at material quantification is to have a model with limited bias and limited noise.

More generally, in statistics and machine learning, the bias—variance tradeoff is the property of a set of predictive models wherein models with a lower bias in parameter estimation have a higher variance of the parameter estimates across samples, and vice versa. The higher variance means more noise but less bias. The higher bias means less noise, but potentially more systematic inaccuracy.

The bias error can be understood as an error from erroneous assumptions in the learning algorithm. High bias can cause an algorithm to miss the relevant relations between features and target outputs (underfitting).

The variance is an error from sensitivity to small fluctuations in the training set. High variance can cause an algorithm to model the random noise in the training data, rather than the intended outputs (overfitting).

Ideally, an AI algorithm output has both low noise and low bias.

The invention is defined by the claims.

According to examples in accordance with an aspect of the invention, there is provided a method for material decomposition of an object using spectral X-ray data for the object, the method comprising:

accessing a data storage arrangement, wherein the data storage arrangement stores a first AI model and a second AI model, each of the first and second AI models configured to receive spectral X-ray data as model input data, and to generate material decomposition data as model output data, and wherein the first AI model is configured to exhibit lower bias than the second AI model and higher variance than the second AI model;

obtaining input spectral X-ray data;

providing the input spectral X-ray data as model input data to the first AI model, and subsequently applying low-pass filtering to the model output data of the first AI model to derive first material decomposition data;

providing the input spectral X-ray projection data as model input data to the second AI model, and subsequently applying high-pass filtering to the model output data of the second AI model to derive second material decomposition data;

linearly combining the first and second material decomposition data to derive third material decomposition data.

Embodiments of the invention are based on the concept of using two trained AI-models for material decomposition: one giving low bias, but high noise in the output material decomposition data and the other giving high bias, but low noise. The outputs of the two models are later combined via a frequency split approach in order to achieve a result with low bias and low noise. The frequency split approach effectively comprises selecting just lower frequency components from the low-bias (high-noise) AI model, selecting higher frequency components from the higher-bias (low-noise) model, and linearly combining them. This can be done with filtering.

In more detail, the low pass filtering extracts or selects just the lower frequency or energy components of the output of the first AI model (with low bias), and the high pass filtering extracts or selects just the higher frequency or energy components of the output of the second AI model (having higher bias). The linear combination of the two provides output material decomposition data which is both low in noise and low in bias. This is based on the assumption that noise has predominantly high spatial frequencies, whereas bias is predominantly a low frequency effect.

Preferably, the method comprises applying low-pass spatial filtering to the model output data of the first AI model. This is preferably applied in at least one dimension of the output data. Low pass spatial filtering means applying a low pass filtering of spatial frequencies of the output material decomposition data.

Preferably, the method comprises applying high-pass spatial filtering to the model output data of the second AI model. This is preferably applied in the same at least one dimension as above. High pass spatial filtering means applying a high pass filtering of spatial frequencies of the output material decomposition data.

For example, the model output data may comprise data values which extend over two or more dimensions. For example, the model output data may comprise material decomposition data values for each of a plurality of pixels of an array of pixels, the pixel array extending in at least two dimensions. For example, the low pass spatial filtering may be for filtering spatial frequency components of the set of model output data in at least one spatial dimension of the data. For example, the high pass spatial filtering may be for filtering spatial frequency components of the set of model output data in said same at least one spatial dimension of the data.

Filtering spatial frequencies means in general that e.g., an image, is decomposed in periodic patterns (which is possible for any image), each periodic pattern is weighted with a weighting factor, and the weighted periodic patterns are then summed to obtain a modified image (the filtered image), where the modification depends upon the weighting. In low pass filtering, high weightings would be applied to higher frequencies of the periodic patterns, and vice versa for high pass filtering. Practically this process can be replaced by a convolution operation which is directly applied to the image. This concept can be applied to 2D or 3D images.

The model output data may comprise data values for each of a set of pixel locations spanning e.g. a 2D or 3D grid, and thus can be understood as an 'image' of material decomposition data. The spatial filtering can therefore be applied to the output data of the two models in a similar way to how it is applied to a standard image.

There are different options in practice for how to implement the spatial filtering of the model output of the first and second AI models. For instance, in one non-limiting example, the model output data may comprise data values (e.g. material path length values, or other values) for each of a set of materials, and for each of a set of views, and for each of a (2D) array of pixels, as a respective 2D 'image' dataset for each view and each material, and wherein the spatial filtering is applied to each of these 2D 'image' datasets. As a variation on this example, a set of 3D image datasets could be formed for each material, each 3D dataset comprising a stack of the previously referenced 2D 'images', the third dimension corresponding to the different views, and wherein the spatial filtering is applied in the 3D domain, i.e. spatial filtering is applied to each of the 3D datasets for each material, e.g. in one or more dimensions of this 3D array of values. In this latter option, it will be understood that the third dimension is not necessarily a physical spatial dimension, and thus the spatial filtering does not have to be applied along a physical spatial dimension, but could be applied to periodic patterns in the output data across another dimension of the output data array. Other options will be apparent to the skilled person in this field.

The two different AI models can be generated either by varying the training data that is supplied to the two models during training (e.g. one is supplied with more noisy data than the other), or by varying the training procedure itself between the two models, e.g. train one model with a different cost function than the other, configured to favor noise. Each of the AI models may comprise one or more machine learning algorithms, for example one or more artificial neural networks.

For avoidance of doubt, it is noted that the first AI model is configured to exhibit lower bias in the output material decomposition data values than the second AI model and higher variance in the output material decomposition data values than the second AI model.

The method is broadly applicable to a wide range of different particular applications. In particular, the type of input X-ray data that is used can vary (e.g. conventional X-ray or CT data) and the type of output material composition data that is generated can vary, e.g. material projection data, or material image data.

Thus, in different examples, the input spectral X-ray data may be spectral projection data (i.e. unreconstructed spectral projection data, e.g. in the form of photon count data for a set of different energy bins) or may be spectral image data (i.e. reconstructed spectral projection data). The input spectral X-ray data may comprise raw projection data as generated by an X-ray scanning apparatus, or may be data which has been pre-processed, for example reconstructed to form spectral image data.

In different examples, the material decomposition data may be material projection data, or may be material image data.

In some examples, the spectral X-ray data may comprise spectral computed tomography, CT, data for the object (including projection data for multiple projection angles). Alternatively, it may comprise conventional X-ray or fluoroscopy data, captured from a single projection angle.

In different examples, the whole process can be done in the projection data domain, or the whole process can be done in the image data domain (by reconstructing the spectral projection data into image data before feeding it to the two AI models), or part of the process can be done in the projection domain and part in the image domain, e.g. the AI models might accept input spectral projection data, and output material projection data, while the frequency filtering part is done in the image domain after reconstruction of the material projection data. The various options will be discussed in more detail to follow.

The first and second AI models may be machine learning models trained using a supervised learning procedure.

According to one or more embodiments, the first AI model may be trained based on training data $T_1$, and second AI model may be trained based on training data $T_2$, and wherein $T_1$ is generated so as to have reduced noise compared to $T_2$. The reduced noise in $T_1$ can be achieved for example by pre-processing the training data so as to have reduced noise compared to $T_2$. For example, the first AI model is trained on training data $T_1$ and the second AI model is trained on training data $T_2$, where $T_1$ is generated by applying noise suppression to $T_2$. However, in other examples, noise might be artificially added to the training data set $T_2$. In other words, the first AI model is trained on training data $T_1$ and the second AI model is trained on training data $T_2$, wherein $T_2$ is generated by adding noise to $T_1$. The noise which is added might be simulated using a random noise generator for example. In further examples, one or both of $T_1$ and $T_2$ may be generated by simulation, i.e. using an X-ray simulation program. Within a simulation, the noise level of the obtained data can be arbitrarily adjusted, so that one or both of $T_1$ and $T_2$ could be obtained in this way.

In this approach, the two AI models may begin as two copies of the same machine learning network or algorithm, but are trained with separate and differing training data to achieve the disparity in their respective bias and variance.

As an alternative to this approach, the learning algorithms comprised by the first and second machine learning models may be configured so as to follow differing learning or training strategies, one which favors lower bias (higher noise) and one which favors lower noise (higher bias).

For example, the first model may be configured to have reduced bias by configuring the first model with a different cost function, so that the cost function of the second model gives more noise and the cost function of the first model gives lower noise.

In accordance with one or more embodiments, each of the first and second AI models is configured to receive spectral X-ray projection data as model input data, and to generate material composition projection data as model output data. Hence here, the material decomposition is done in the projection data domain.

The method may for example be a basis material decomposition method, and wherein the output material decomposition data comprises a set of derived radiation path lengths, $l_s$, through a scanned material for each of a set of basis materials having known attenuation coefficients. Here the output material decomposition data comprises material projection data. In other words, it is unreconstructed material decomposition data, as opposed for example to image data.

Where the input spectral X-ray data is spectral CT data, the output material decomposition data may comprise a path length sinogram vector $t(p, v)$, comprising the derived basis material path lengths for each of the set of basis materials, for radiation arriving at each of a set of pixels p of the detector and for each of a set of projection views, v, of the input spectral X-ray data.

A sinogram is a visual representation of the raw data obtained in the operation of computed tomography. A path length sinogram is a visual representation of the material basis path lengths for each pixel of the detector.

In accordance with one or more embodiments, the method may further comprise applying an image reconstruction operation to the first and second material decomposition data, either before or after their linear combination, such that the output material decomposition data comprises output material image data.

Material image data refers to a visual or graphical representation of the material decomposition information. For example, material image data may comprise a set of images, each image representing one material. A further option is to represent different materials in an imaged area using color-coding in a single image (e.g., each material is represented with a dedicated color).

According to one or more embodiments, the input spectral X-ray data may comprise projection data, e.g. spectral photon count data $c_s$, indicative of a detected X-ray photon count in each of a plurality of energy bins at an X-ray detector.

In accordance with a further set of embodiments, each of the first and second AI models may be configured to receive spectral X-ray image data as model input data and to generate material decomposition image data as model output data. Hence here, the material decomposition is done in the image domain instead of the projection domain.

As mentioned above, in accordance with one or more embodiments, the input spectral X-ray data may be spectral CT data. This may be spectral CT projection data or may be spectral CT image data in different examples. Alterative to CT data, the input spectral X-ray data may be conventional spectral X-ray data.

In accordance with this set of examples, the input spectral X-ray data may comprise spectral photon count data $c_s(p, v)$ indicative of a detected X-ray photon count in each of a plurality of energy bins at an X-ray detector, and for each of a plurality of pixels, p, and for each of a plurality of projection views, v of the input spectral X-ray data.

Examples in accordance with a further aspect of the invention provide a computer program product comprising computer program code, the computer program code being executable on a processor or computer, wherein the code is configured to cause the processor to perform a method in accordance with any example or embodiment outlined above or described below, or in accordance with any claim of this application.

Examples in accordance with a further aspect of the invention provide a processing arrangement for processing spectral X-ray data to derive material decomposition information, the processing arrangement configured to:

access a data storage arrangement, wherein the data storage arrangement stores a first AI model and a second AI model, each of the first and second AI models configured to receive spectral X-ray data as model input data, and to generate material decomposition data as model output data, and wherein the first AI model is configured to exhibit lower bias than the second AI model and higher variance than the second model;

obtain input spectral X-ray data;

provide the input spectral X-ray data as model input data to the first AI model, and subsequently apply low-pass filtering to the model output data of the first AI model to derive first material decomposition data;

provide the input spectral X-ray data as model input data to the second AI model, and subsequently apply high-pass filtering to the model output data of the second AI model to derive second material decomposition data;

linearly combine the first and second material decomposition data to derive third material decomposition data.

In accordance with some embodiments, the processing arrangement may comprise the data storage arrangement storing the first and second AI models.

Examples in accordance with a further aspect of the invention provide an X-ray imaging system, comprising:

an X-ray scanning assembly comprising an X-ray radiation source and an X-ray radiation detector with a scanning area between the two for receiving an object to be scanned, wherein an X-ray radiation path between the source and detector passes through the scanning area; and a processing arrangement in accordance with any example or embodiment outlined above or described below, or in accordance with any claim of this application. The processing arrangement is communicatively coupled to the X-ray radiation detector to receive input spectral X-ray data from the X-ray detector.

The scanner assembly may be a CT-scanning assembly. It may therefore be arranged to enable an adjustable angular positioning of the X-ray source relative to the X-ray detector.

The X-ray detector may be an X-ray photon counting detector adapted to detect photon counts for each of a set of radiation frequency or energy bins.

Examples in accordance with a further aspect of the invention provide a method of training a first and second AI model for use in deriving material decomposition data from input spectral X-ray data. The method comprises:

obtaining a preliminary AI model configured to obtain spectral X-ray data as model input data, and to generate material decomposition data as model output data;

training a first copy of the preliminary AI model with first training data, $T_1$, to thereby obtain a first AI model;

training a second copy of the preliminary AI model with second training data $T_2$, to thereby obtain a second AI model;

wherein each of the first and second training data comprise input data entries in the form of sample spectral X-ray data, and corresponding output data entries in the form of known material decomposition data for each of the sample spectral X-ray data, and wherein the first training data $T_1$ is generated or pre-processed so as to have reduced noise in the spectral X-ray data forming its input data entries, such that the first training data has reduced noise compared to the second training data.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 1 outlines in block diagram form steps of an example method according to one or more embodiments;

FIG. 2 illustrates comparative results for material decomposition obtained using an embodiment of the invention;

DETAILED DESCRIPTION OF THE EMBODIMENTS

Figure 3:
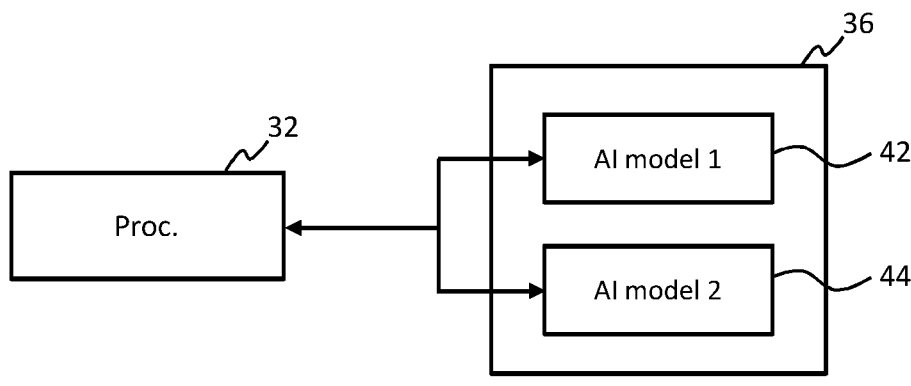
FIG. 3 shows an example processing arrangement for implementing a method according to one or more embodiments of the invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Embodiments of the invention provide a method for material decomposition of an object based on spectral X-ray scan data for the object and based on application of AI models and a frequency split approach. The method comprises using two AI models in parallel to perform the material decomposition based on input spectral X-ray data, wherein the models are configured so that one exhibits higher bias and lower variance (lower noise) than the other. The input spectral X-ray data is fed to both models. The output material composition data from the low bias model is low pass filtered and the output material composition data from the low variance model is high pass filtered. The outputs from the two models are linearly combined. The resulting combined material decomposition data has both lower bias and lower noise compared to the output generated if just one AI model were to be used.

By using multi-energy X-ray detectors, it is possible to measure the spectrum of X-ray energies or frequencies received at different locations across an X-ray detector during X-ray imaging of an object. This is known as spectral X-ray imaging. Spectral X-ray data allows for discerning and quantifying materials comprised by the scanned object. It can be performed using data from a conventional X-ray imaging modality or from CT imaging.

Material decomposition can be achieved based on a pixel-wise inversion of the system forward model, which model describes the theoretical signal expected in individual X-ray detector energy bins as a function of a certain set (basis) of materials comprised by the object and their respective equivalent path lengths. This procedure is called basis material decomposition.

Material decomposition using spectral photon counting X-ray data is a non-linear, ill-posed and computationally expensive problem. Using AI-models for decomposition can help to reduce the computation time considerably, but the ill-posed nature of the problem can still lead to strong noise amplification and bias in the output of the AI-model.

According to embodiments of the present invention, a decomposition method using two or more AI-models is proposed to reduce bias and noise. It utilizes a frequency split concept, based on the assumption that noise has high spatial frequencies in the projection domain, and the image domain, while bias is a low frequency effect.

The basic principles of spectral x-ray based material decomposition, as applied in embodiments of the present invention, will now be briefly discussed. A more detailed discussion of the underlying principles of material decomposition applied herein can also be found in the paper: K. C. Zimmerman and T. G. Schmidt, Experimental comparison of empirical material decomposition methods for spectral CT, Physics in Medicine & Biology, 60 (2015) 8.

When an x-ray photon strikes a photon-counting detector, the photon is converted to electrical charge proportional to the energy of the incoming photon. The charge may be converted to a voltage using charge-integrating amplifiers.

Analog comparators can be used to increment a digital counter when the voltage of the accumulated charge exceeds a set threshold level. At the end of an acquisition, the number of photons detected with energy above the threshold can be counted. Energy bin data can be generated corresponding to the number of photons detected between two threshold levels based on subtracting consecutive counter measurements. In this way, a photon count for a plurality of x-ray energy bins can be generated.

It is noted that for the purpose of the following description, use of a spectral photon counting detector will be assumed. However, other types of detector are also possible such as spectral energy integrating detectors (EIDs) which are able to detect radiation within a particular window of the energy spectrum of the X-ray source.

The case may be considered of an x-ray measurement through a material of thickness x and attenuation coefficient $\mu(E)$, where E is the energy of photon traversing the material. The x-ray attenuation of a composite material can be expressed as a linear combination of the attenuation of a set of basis materials comprised by the material. More particularly, and as explained in K. C. Zimmerman (2015), the x-ray attenuation through this material is equivalent to the attenuation of a unique combination of any two other materials (in the absence of K-edges), as expressed in equation (1) below, where $\mu_1(E)$ and $\mu_2(E)$ are the energy-dependent attenuation coefficients of each of two basis material and $l_1$, and $l_2$ are the path lengths of each of the two basis materials. This decomposition is possible because there exist two primary attenuation phenomena in the diagnostic x-ray energy range: Compton scattering and photoelectric absorption.

$$x\mu(E)=l_1\mu_1(E)+l_2\mu_2(E) \tag{1}$$

This basis expansion can be extended, so that the expected number of photons detected in the $i^{th}$ energy bin, $c_i$, of an ideal photon-counting detector can be modelled as, $$c_i(l) = \int\limits_{E_i}^{E_{i+1}} S(E)\exp\left[-\sum_{j=1}^{M}l_j\mu_j(E)\right]dE \tag{2}$$

where S(E) is the x-ray source spectrum and $l_j$, the elements of l, are the thicknesses of M basis materials having attenuation coefficients functions, $\mu_j$. The spectral measurements are represented as a vector of detected photon counts, $c=[c_1, c_2, \ldots, c_K]^T$, where K is total the number of energy measurements.

Material decomposition in general terms involves estimating the basis material thicknesses, l, from the acquired spectral data, c. One method of estimating the basis material thicknesses, l, from the number of detected photons, c, is to numerically invert equation (2), for example using statistical estimation algorithms such as maximum likelihood estimation, (MLE). However, this can lead to over-simplification, unable to account for real-word detector effects such as pulse pileup and charge sharing.

Another approach, which can overcome some of these problems is artificial intelligence (AI) model-based approaches. It is this approach which is used in embodiments of the present invention.

According to embodiments of the present invention, in order to perform basis material decomposition in the projection domain, a machine learning algorithm, such as neural network, can be employed which is trained using energy bin data from known thicknesses of the basis materials. For example, a database of various reference path length vectors l($p$) for the given material basis of interest is generated along with the resulting photon count data vectors c($p$), both functions of pixel p of the detector.

The trained AI model, f, is configured to estimate the basis material thicknesses of a scanned object from the spectral x-ray measurements. This may be expressed as follows:

$$\hat{l}(p)=f(p),c_s(p)) \tag{3}$$

where $\hat{t}$ is the computed path length vector for the basis materials, for pixel p, and w(p) is the weighting parameter vector of the AI-model f for pixel p. In the case that the input spectral data c is CT data, the computed path length data may be a sinogram vector $r_c(p, v)$, which is a function of the detector pixel, p, and the projection view, v, acquired during the scan.

The training of the AI model f can be based on use of the database of reference path length vectors l(p) and photon counts discussed above, and based on training the AI model for each pixel in the database, such that the resulting AI-model f minimizes the error, Er, between the predicted path lengths (the output of the model) and the true path lengths:

$$\hat{w}(p)=\text{argmin } Er(l(p)-f(w(p),c(p))) \tag{4}$$

The above principles may be applied in accordance with the various embodiments of the present invention. A number of embodiments of the invention will now be discussed in more detail.

FIG. 1 outlines in block diagram form steps of an example method according to one or more embodiments for material decomposition of an object using spectral X-ray data for the object.

The method comprises accessing 12 a data storage arrangement. The data storage arrangement stores a first AI model and a second AI model. Each of the first and second AI models is configured to receive spectral X-ray data as model input data, and to generate material decomposition data as model output data.

The first AI model is configured to exhibit lower bias than the second AI model. The first AI model is configured to exhibit and higher variance than the second AI model.

The method further comprises 14 obtaining input spectral X-ray data. This may be input projection data or may be reconstructed spectral image data. The input X-ray data may be obtained directly from an X-ray scanning apparatus, e.g. for real-time processing. It may be obtained from a datastore, e.g. for offline processing. It may be obtained from a processing component or unit configured to pre-process the data, for example from a reconstructor which receives the raw projection data and outputs reconstructed spectral image data. In this way, the form of the spectral X-ray data received and supplied as input to the two AI models may vary in different embodiments.

The method further comprises providing 16 the input spectral X-ray data as model input data to the first AI model.

The method further comprises providing 18 the input spectral X-ray projection data as model input data to the second AI model.

The method further comprises 20 applying low-pass filtering to the model output data of the first AI model, and applying high-pass filtering to the model output data of the second AI model.

For the low pass filtering, any linear low pass filter may be used. For instance, by way of non-limiting example, a moving average filter, Gaussian window filter, Hann window filter, Hamming window filter, Kaiser window filter, or any other suitable example low pass filter as will be apparent to the skilled person.

For the high pass filtering, again, any suitable high pass filter may be used as will be apparent to the skilled person. By way of non-limiting example, the high pass filtering may be done using a Dirac pulse minus the low pass filter, or for instance by low pass filtering the data and then subtracting low pass filtered data from the original data.

The method further comprises linearly combining 22 the outputs of the first and second AI models to derive output material decomposition data. The linear combining can be done after the model outputs have been filtered.

The combination of the filtering of the model outputs and linearly combining them (as outlined above) may be referred to as a frequency split approach or frequency split procedure. This terminology may be used herein for brevity.

Optionally, the method may further comprise a reconstruction step, comprising applying an image reconstruction operation to the outputs of the first and second AI models, either before or after their filtering and/or their linear combination, such that the output material decomposition data comprises output material image data.

Material image data refers to a visual or graphical representation of the material decomposition information. For example, material image data may comprise a set of images, each image representing one material. A further option is to represent different materials in an imaged area using color-coding in a single image (e.g., each material is represented with a dedicated color).

In different embodiments of the invention, the AI models may be configured to receive input spectral X-ray data in different forms, and to generate output material composition data of different forms. For example, the input data can be projection data or it can be reconstructed image data, and the output material composition data from the models can be in the projection domain (material projection data) or it can be in the image domain (material image data).

Four of the main different advantageous options will be briefly outlined below:

(1) The input spectral X-ray data is data from a conventional X-ray modality system. Here, acquired spectral X-ray projection data is decomposed with the two AI models to achieve two sets of output material projection data. These two sets of material projection data are combined with the frequency split step discussed above to arrive at final material projection data. This provides the output material decomposition data. This can be used directly for visualization in some examples.

(2) The spectral X-ray data is data from a computed tomography (CT) system. The acquired spectral X-ray projection data is provided as the input data to the two AI models. It is decomposed with the two AI models to derive two sets of output material projection data. The material projection data may for example comprise a vector of the material paths lengths in the scanned object of a set of basis materials. These two sets of material projection data are combined with the frequency split step discussed above (filtering and linearly combining) to derive final material projection data. Optionally, this may be subsequently processed with a reconstruction procedure to derive final material image data.

(3) The input spectral X-ray data is data from a computed tomography (CT) system. The acquired spectral X-ray projection data is provided as input data to the two AI models. The data is decomposed with the two AI models to derive two sets of material projection data. These two sets of material projection data are then both reconstructed to derive two sets of material image data. These image data sets are combined with the frequency split step (filtering and linearly combining) as discussed above, to derive the final material image data.

(4) The spectral X-ray data is data from a computed tomography (CT) system. The acquired spectral X-ray projection data is reconstructed to derive a set of spectral image data as the input spectral X-ray data. This is provided as the input data to the two AI models. The spectral image data is decomposed with two AI models to derive two sets of material image data, which are then combined with the frequency split procedure discussed above (filtering and linearly combining) to derive final material image data.

As can be seen, options (2)-(4) differ in the order of the various processing steps (decomposition/frequency split/reconstruction). Option (1) does not have the reconstruction step.

To achieve the results of the method, two AI models are needed which are both capable of material decomposition, but differ in their exhibited bias and variance.

Each of the AI models may comprise one or more machine learning algorithms.

A machine-learning algorithm is any self-training algorithm that processes input data in order to produce or predict output data. Here, the input data comprises spectral X-ray data and the output data comprises material decomposition data.

Suitable machine-learning algorithms for being employed in the present invention will be apparent to the skilled person. Examples of suitable machine-learning algorithms include decision tree algorithms and artificial neural networks. Other machine-learning algorithms such as polynomial regression, support vector regression or kernel regression are suitable alternatives.

The structure of an artificial neural network (or, simply, neural network) is inspired by the human brain. Neural networks are comprised of layers, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can be repeated until the error converges, and the predicted output data entries are sufficiently similar (e.g. ±1%) to the training output data entries. This is commonly known as a supervised learning technique.

For example, where the machine-learning algorithm is formed from a neural network, (weightings of) the mathematical operation of each neuron may be modified until the error converges. Known methods of modifying a neural network include gradient descent, backpropagation algorithms and so on.

The training input data entries correspond to example input spectral X-ray data for a given material basis (e.g. sample photon energy bin counts for the material basis). The training output data entries correspond to material decomposition data.

As discussed, in different embodiments of the invention, the AI model may be configured to receive input X-ray data in different forms, and to generate output material composition data of different forms. For example, the input data can be projection data or it can be reconstructed image data, and the output material composition data from the models can be in the projection domain (material projection data) or it can be in the image domain (material image data).

To better understand the principles of the invention an example will be described in more detail in which the input data to the AI models is CT projection data, and the output material decomposition data from the AI models is decomposition projection data. However, the same principles can be applied for models which input and output the data in different forms.

In accordance with the present examples, the decomposition method is a basis material decomposition method. The final output material decomposition data in this case comprises a set of derived radiation path lengths, $l_s$, through a scanned material for each of a set of basis materials having known attenuation coefficients. The theory behind this approach was discussed in more detail above, and we refer the reader to this explanation for more detail.

The final output material decomposition data may comprise for example a path length sinogram vector $l(p, v)$, comprising the derived basis material path lengths for each of the set of basis materials, for radiation arriving at each of a set of pixels p and for each of a set of projection views, v, of the input spectral X-ray data.

As discussed above, basis material decomposition in the projection domain requires effectively inverting of the system forward model (e.g. in a form similar to equation (2) above), which models the expected photon counts in individual detector energy bins as a function of the respective basis and equivalent path lengths, for each pixel element of the x-ray projection data. Machine learning algorithms such as neural networks, can be trained to perform this inversion.

For training the AI models, a reference database can be employed of various path length vectors l(p) for the given material basis of interest, along with the resulting photon count data vectors c(p), both functions of pixel p. The AI model is then trained for each pixel in the database, such that the resulting AI-model f minimizes the error, Er, between the predicted path lengths (the output of the model) and the true path lengths, with w (p) being the parameter vector of the AI-model f for pixel p:

$$\hat{w}(p) = \operatorname{argmin} Er(l(p) - f(w(p), c(p))) \qquad (5)$$

The training database can be generated experimentally using calibration phantoms or may for example be generated based on performing realistic system simulations. Once trained, the model can be applied to the photon count projection data $c_s(p, v)$ of each projection view v acquired during the scanning to estimate the equivalent path length sinogram $\widehat{l_s}(p, v)$:

$$\widehat{l_s}(p, v) = f(\hat{w}(p), c_s(p, v)) \qquad (6)$$

As mentioned earlier, the resulting trained model will aim at a compromise in terms of output path length bias and noise, leading to some level of both phenomena. The aim according to embodiments of the present invention is to provide an overall method that achieves both low bias and low noise.

To this end, and as discussed, the first AI model is configured so as to exhibit lower bias than the second AI model and higher variance than the second AI model. In the present context, the bias error may be understood as a deviation of the average of the estimated output path lengths of an AI model from true path lengths. The variance error may be understood as the variability of the aforementioned model output path length estimates with respect to the true path length.

There are different ways of achieving a first AI model which exhibits lower bias than the second AI model and higher variance than the second AI model.

One way is to initially generate two copies of a preliminary network f, and to train the two copies on two different types of photon count data: one without noise, and one with the full noise expected during a typical X-ray or CT scan. For example, two copies of an initial training data set could be generated, and then one of the datasets is pre-processed to reduce noise. The lower noise data is used to train the first AI model and the full noise data is used to train the second AI model. As a result of the training with the noiseless data, a first AI model is achieved with low bias and high noise (high variance): $(f_1(\hat{w}_1(p), c(p, v)))$. The training with the noisy data on the other hand results in a second AI model with high bias and low noise (low variance): $(f_2(\hat{w}_2(p), c(p, v)))$.

An alternative way to achieve the difference in bias and variance between the two AI models is to use the same training data for both, but to change the training strategy employed by the two models, i.e. vary the learning algorithms encoded in the models so that one model favors lower bias, the other favors lower noise (lower variance). For example, the first model may be configured to have reduced bias by configuring the first model with a different cost function, so that the cost function of the second model gives more noise and the cost function of the first model gives lower noise. Both models are then trained using the full-noise training data.

For example, in accordance with one or more embodiments, the occurring bias can be calculated during the training of a given model, and the absolute value of the bias used as one term in the cost function. The more weight that is given to this term, the lower the bias of the trained model. Thus, a higher weight can be given to this term in the cost function when training first AI model.

The bias can be calculated during training if, for example, within the set of training data for a given combination of materials, several (example) noisy realizations of photon counts are available for reference.

Bias and variance of AI models, e.g. neural networks, are measurable, testable properties. Measuring the bias and variance of a given model, where the model is trained for generating output material decomposition information based on input spectral X-ray data, can be done for example empirically by scanning a phantom with inserts featuring different known material concentrations (e.g. iodine or water), and generating corresponding spectral X-ray data for the phantom.

By feeding this input spectral X-ray data to the model being tested, bias can be measured as the deviation of the mean concentration value, measured in the corresponding image region-of-interest (ROI) with respect to the known concentration. Noise or variance can be quantified as the standard deviation of values measured in a homogenous part of each of the material images.

As discussed above, following the decomposition performed by the two AI models, a 'frequency split' step is applied which comprises a combination of selective filtering of the outputs of the first and second AI models, and linearly combining their results.

In particular, in the context of the above outlined examples in which the input spectral X-ray data is spectral CT projection data, it may comprise combining the individual path length sinograms resulting from the application of the $f_1$ and $f_2$ model respectively, after filtering the model outputs using a linear low pass (G) and a matching linear high pass filter (1-G), respectively:

$$\hat{l}_s(p,v)=G(f_1(\hat{w}_1(p),c_s(p,v))+(1-G)\{f_2\}\hat{w}_2(p)(p,v))\} \qquad (7)$$

The resulting combined sinogram vector $\hat{l}_s$ provides the output material decomposition data, in this case in the form of output material projection data (a sinogram vector representing the material paths lengths for each pixel and each projection view, for the given material basis).

The resulting combined path length sinogram, $\hat{l}_s$ will then exhibit both low bias and low noise.

By way of illustration, example simulated results of the material decomposition method according to an embodiment of the present invention is shown in FIG. 2. This shows in the first column the true material decomposition image of an iodine sample (upper row) and a water sample (lower row). The second, third and fourth columns show, respectively, image reconstructions of the material decomposition sinogram data resulting from the decomposition applied by the first AI model $f_1$ only, the second AI model $f_2$ only, and the full combined decomposition method according to the present invention, including the frequency split method. As discussed, the first model, $f_1$, is a bias-optimal model (low bias), the second model $f_1$ is a noise optimal model (low noise). It can be seen that the result from the combination of the two models (fourth column) yields the best results, with bias and noise levels comparable to the those provided by the bias-optimal ($f_1$) and noise-optimal ($f_2$) models, respectively.

The above explanation has been outlined in terms of training an AI model which receives spectral CT data in the projection domain (projection data), and which outputs material decomposition data also in the projection domain, i.e. in terms of a vector of path lengths $\hat{l}_s$ (p, v) for the given material basis.

However, the same principles can be applied in similar fashion for training and using AI models which receive spectral X-ray data in different forms, and output decomposition information in different forms. To derive these models, the training data simply needs to be appropriately selected, so that the training input data entries are of the correct modality or form, and the training output data entries are material composition data of the right form.

For example, in various embodiments, the input spectral X-ray data provided to each AI model may be spectral computed tomography (CT) data, as in the above outlined example, or in further embodiments, it may be spectral X-ray data from a conventional (non-CT) X-ray or fluoroscopy scanner. In the latter case, the input spectral X-ray data to the AI models may be in the form of photon count projection data $c_s(p)$, giving photon counts for each energy bin, as a function of the pixel of the detector. Since there may be only one view for a conventional X-ray scanner, the photon count data may be a function of the pixels only. In alternative cases still, the conventional spectral X-ray data might be reconstructed into image data before application of the AI models, and the AI models may be trained to receive the input spectral image data and output material image information.

When the input spectral X-ray data is spectral CT data, the two AI models may be configured to receive input spectral CT projection data, or may be configured to receive reconstructed spectral CT image data, reconstructed from the raw spectral projection data. In the former case, the AI models are trained to output material decomposition data in the projection domain; in the latter case the models are trained to output material composition data in the image domain.

Examples in accordance with a further aspect of the invention provide a computer program product comprising computer program code, the computer program code being executable on a processor or computer wherein the code is configured to cause the processor to perform a method in accordance in accordance with any example or embodiment outlined above or described below, or in accordance with any claim of this application.

FIG. 3 shows components of an example apparatus for performing a material decomposition method in accordance with embodiments disclosed herein.

In particular, an aspect of the invention provides a processing arrangement 32 for processing spectral X-ray data to derive material decomposition information. In this example, the processing arrangement comprises a single processor component, e.g. an Integrated Circuit (IC).

The processing arrangement 32 is configured to access a data storage arrangement 36. The data storage arrangement stores a first AI model 42 and a second AI model 44. Each of the first and second AI models is configured to receive spectral X-ray data as model input data, and to generate material decomposition data as model output data. The first AI model 42 is configured to exhibit lower bias than the second AI model 44 and higher variance than the second AI model.

The processing arrangement is configured to obtain input spectral X-ray data, e.g. from an X-ray scanning apparatus communicatively coupled with the processing arrangement, or from a further datastore in other examples.

The processing arrangement 32 is configured to provide the input spectral X-ray data as model input data to the first AI model 42, and subsequently apply low-pass filtering to the model output data of the first AI model to derive first material decomposition data.

The processing arrangement 32 is configured to provide the input spectral X-ray data as model input data to the second AI model 44, and subsequently apply high-pass filtering to the model output data of the second AI model to derive second material decomposition data.

The processing arrangement 32 is configured to linearly combine the first and second material decomposition data to derive third material decomposition data.

According to one or more embodiments, the processing arrangement 32 may include the data storage arrangement 36 storing the first 42 and second 44 AI models. In other examples, it may comprise an input/output for connecting to the data storage arrangement.

Figure 4:
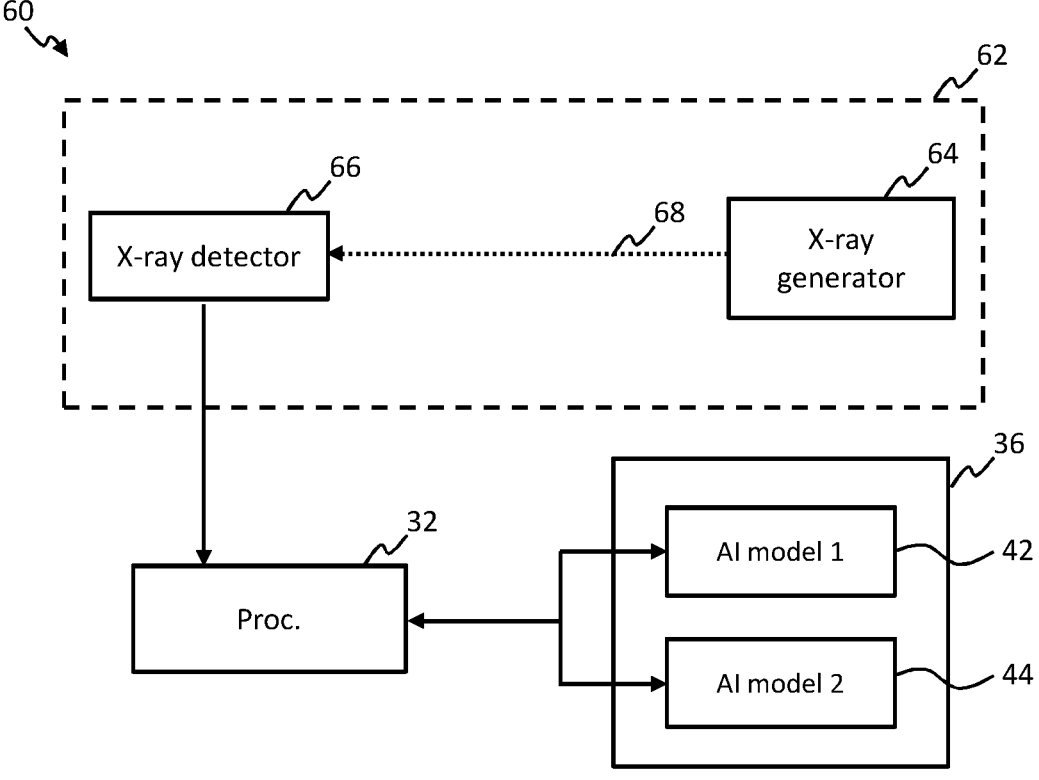
FIG. 4 schematically illustrates an example X-ray system for material decomposition of a scanned object.

Examples in accordance with a further embodiment provide a spectral X-ray system. An example system 60 is shown schematically in FIG. 4.

The system comprises an X-ray scanning assembly 62 comprising an X-ray radiation source 64 (X-ray generator) and an X-ray radiation detector 66 with a scanning area between the two for receiving an object to be scanned, wherein an X-ray radiation path 68 between the source and detector passes through the scanning area.

The system further comprises a processing arrangement 32, in accordance with any example or embodiment outlined above or described below, or in accordance with any claim of this application. The processing arrangement is communicatively coupled to the X-ray radiation detector 66 to receive input spectral X-ray data from the X-ray detector.

The X-ray scanning assembly 62 may be a CT scanning assembly, wherein the radiation source 64 and radiation detector 66 have an adjustable relative angular positioning, to thereby enable multiple projection views, corresponding to different X-ray path angles through the scanning area, to be captured.

In preferred examples, the X-ray detector 66 is an X-ray photon counting detector adapted to detect photon counts for each of a set of radiation frequency or energy bins.

Alternatively, the X-ray detector 66 may comprise one or more energy integrating detectors (EIDs). EIDs are capable of selectively sensing incident X-Ray radiation of a chosen window of radiation. In one possible arrangement, two or more EIDs are used in a stack or dual-layer configuration, each configured to be sensitive to a different energy window of the x-ray spectrum of the X-Ray source (e.g. an X-Ray tube).

In a further possible arrangement, a single EID is used, and wherein the X-Ray source is controlled to cycle through two or more different X-Ray tube voltages so as to sequentially emit radiation of different energy spectra. The single EID detects the radiation associated with each tube voltage in turn. Thus the energy level of the radiation is controlled at the source, rather than being discriminatively detected at the detector in this case.

The basic architecture of a suitable X-Ray scanning assembly for use in embodiments of the present invention is described for example in WO 2014/167450 between page 3, line 26 and page 5, line 2, and shown in FIG. 1 of that document. The radiation detector array may take the form of a photon counting detector or one or more energy integrating detectors for instance.

Further details on the construction, operation and implementation of suitable X-Ray scanning assemblies can also be found in the book: "Spectral, Photon Counting Computed Tomography (Technology and Applications)" by Katsuyuki Taguchi (2020).

Details on the key principles of suitable CT scanning assemblies may also be found in the paper: Willemink, M et al, "Photon-counting CT: Technical Principles and Clinical Prospects" (2018).

As discussed above, one means for obtaining the two AI models having different bias and variance is by training the two models with different training data.

Figure 5:
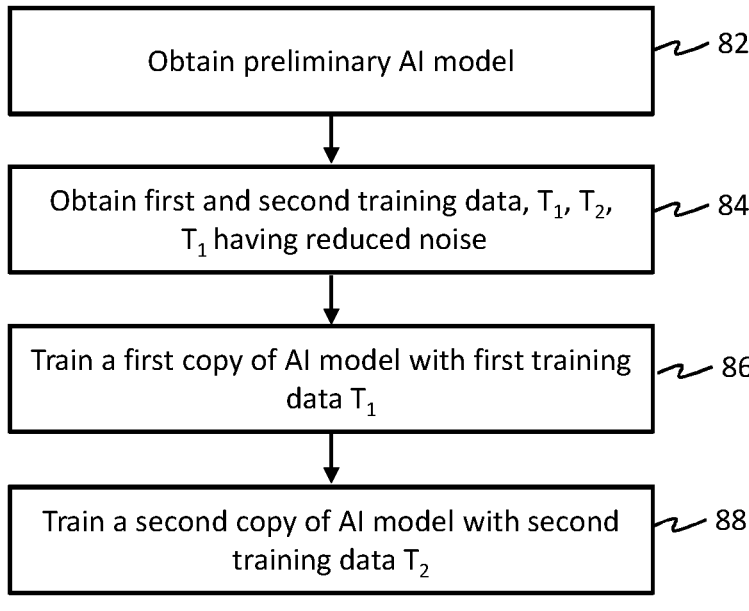
FIG. 5 outlines steps of an example method for training two AI models for use in material decomposition based on spectral X-ray data.

Thus, examples in accordance with a further aspect of the invention provide a method of training a first and second AI model for use in deriving material decomposition data from input spectral X-ray data. FIG. 5 outlines, in block diagram form, steps of an example of such a method.

The method comprises obtaining 82 a preliminary AI model configured to receive spectral X-ray data as model input data, and to generate material decomposition data as model output data.

The method further comprises obtaining 84 first, $T_1$, and second, $T_2$, training data, wherein each of the first and second training data comprise input data entries in the form of sample spectral X-ray data, and corresponding output data entries in the form of known material decomposition data for each of the sample spectral X-ray data. The first training data $T_1$ is provided having reduced noise in the spectral X-ray data forming its input data entries compared to $T_2$, such that the first training data has reduced noise compared to the second training data. This may be achieved for example by pre-processing the first training data to reduce noise. For example, $T_1$ may be generated by applying noise suppression to a second copy of $T_2$. It may alternatively be achieved by pre-processing the second training data to have additional noise (compared to $T_1$). In other words, noise might be artificially added to the training data set $T_2$. In other words, $T_2$ is generated by adding noise to a second copy of $T_1$. The noise which is added might be simulated using a random noise generator for example. In further examples, one or both of $T_1$ and $T_2$ may be generated by simulation, i.e. using an X-ray simulation program. Within a simulation, the noise level of the obtained data can be arbitrarily adjusted, so that one or both of $T_1$ and $T_2$ could be obtained in this way.

The method further comprises training 86 a first copy of the preliminary AI model with first training data, $T_1$, to thereby obtain a first AI model.

The method further comprises training 88 a second copy of the preliminary AI model with second training data $T_2$, to thereby obtain a second AI model.

The result is that the first AI model is obtained having less bias and greater variance that the second model.

Although in the above example, the two models begin as copies of the same preliminary model, this is not essential. In further embodiments, a first preliminary model may be trained with the first training data, $T_1$, to obtain the first AI model and a second preliminary model may be trained with the second training data, $T_2$, to thereby obtain a second AI model, where the first and second preliminary models may be different. For example, one preliminary model might be a neural network and the other a linear regression model. The use of the different training data to train the preliminary models (in the manner outlined above) will still result in the differing bias and variance of the two models.

As discussed above, an alternative way to achieve the difference in bias and variance between the two AI models is to use the same training data for both, but to change the training strategy employed by the two models, i.e. vary the learning algorithms encoded in the models so that one model favors lower bias, the other favors lower noise (lower variance).

Embodiments of the present invention have broad application in a variety of different areas. For example, the method and system could be used in processing medical imaging data, for example medical CT data. Material decomposition in the medical field is frequently used for example for analyzing the composition of tumors to determine if tissue is cancerous. However, embodiments could also be used outside of the medical field, for example for analyzing the material composition of inanimate objects.

As discussed above, the system makes use of processor to perform the data processing. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A computer-implemented method for material decomposition of an object using spectral X-ray data for the object, the method comprising:

accessing a data storage, wherein the data storage stores a first AI model and a second AI model, each of the first and second AI models configured to receive spectral X-ray data as model input data, and to generate material decomposition data as model output data, and wherein the first AI model is configured to exhibit lower bias and higher variance in the output material decomposition data values than the second AI model, wherein the first AI model is trained using first training data having reduced noise, and the second AI model is trained using second training data having greater noise than the first training data, such that the first AI model exhibits lower bias and higher variance than the second AI model;

obtaining input spectral X-ray data;

providing the input spectral X-ray data as model input data to the first AI model;

providing the input spectral X-ray data as model input data to the second AI model;

applying low-pass spatial filtering to the model output data of the first AI model to generate first filtered output data;

applying high-pass spatial filtering to the model output data of the second AI model to generate second filtered output data; and linearly combining the first filtered output data and the second filtered output data to obtain output material decomposition data.

2. The method as claimed in claim 1, wherein each of the first and second AI models is configured to receive spectral X-ray projection data as model input data, and to generate material decomposition projection data as model output data.

3. The method as claimed in claim 2, wherein the output material decomposition data comprises a set of derived radiation path lengths through a scanned material for each of a set of basis materials having known attenuation coefficients.

4. The method as claimed in claim 3, wherein the output material decomposition data comprises a path length sinogram vector comprising the derived basis material path lengths for each of the set of basis materials, for radiation arriving at each of a set of pixels and for each of a set of projection views of the input spectral X-ray data.

5. The method as claimed in claim 2, further comprising applying an image reconstruction operation to the first and second material decomposition data, either before or after their linear combination, such that the output material decomposition data comprises output material image data.

6. The method as claimed in claim 2, wherein the input spectral X-ray data is projection data and comprises spectral photon count data indicative of a detected X-ray photon count in each of a plurality of energy bins at an X-ray detector.

7. The method as claimed in claim 1, wherein each of the first and second AI models is configured to receive spectral X-ray image data as model input data and to generate material decomposition image data as model output data.

8. The method as claimed in claim 1, wherein the input spectral X-ray data is spectral CT data.

9. The method as claimed in claim 8, wherein the input spectral X-ray data comprises spectral photon count data indicative of a detected X-ray photon count in each of a plurality of energy bins at an X-ray detector, and for each of a plurality of pixels and for each of a plurality of projection views of the input CT projection data.

10. A spectral X-ray imaging system for material decomposition of an object, comprising:

an X-ray scanning assembly comprising an X-ray source and an X-ray detector with a scanning area between the X-ray source and the X-ray detector for receiving an object to be scanned, wherein an X-ray radiation path between the X-ray source and the X-ray detector passes through the scanning area; and a processor communicatively coupled to the X-ray detector to receive input spectral X-ray data from the X-ray detector, wherein the processor is configured to execute a plurality of instructions to:

access a data storage, wherein the data storage stores a first AI model and a second AI model, each of the first and second AI models configured to receive spectral X-ray data as model input data, and to generate material decomposition data as model output data, and wherein the first AI model is configured to exhibit lower bias and higher variance in the output material decomposition data values than the second AI model, wherein the first AI model is trained using first training data having reduced noise, and the second AI model is trained using second training data having greater noise than the first training data, such that the first AI model exhibits lower bias and higher variance than the second AI model;

obtain the input spectral X-ray data;

provide the input spectral X-ray data as model input data to the first AI model;

provide the input spectral X-ray data as model input data to the second AI model;

apply low-pass spatial filtering to the model output data of the first AI model to generate first filtered output data;

apply high-pass spatial filtering to the model output data of the second AI model to generate second filtered output data; and linearly combine the first filtered output data and the second filtered output data to obtain output material decomposition data.

\* \* \* \* \*